(12) United States Patent
Liu et al.

(10) Patent No.: US 9,693,715 B2
(45) Date of Patent: Jul. 4, 2017

(54) OPTICAL SENSOR FOR DETECTING CHEMICAL, BIOCHEMICAL OR BIOLOGICAL SUBSTANCES

(71) Applicant: Technische Universität Berlin, Berlin (DE)

(72) Inventors: Anjin Liu, Berlin (DE); Werner Hofmann, Berlin (DE); Dieter Bimberg, Berlin (DE)

(73) Assignee: Technische Universität Berlin, Berlin (DE)

( * ) Notice: Subject to any disclaimer, the term of this patent is extended or adjusted under 35 U.S.C. 154(b) by 237 days.

(21) Appl. No.: 14/559,456

(22) Filed: Dec. 3, 2014

(65) Prior Publication Data
US 2016/0161331 A1  Jun. 9, 2016

(51) Int. Cl.
| | | |
|---|---|---|
| *G01J 1/04* | (2006.01) |
| *G01N 21/27* | (2006.01) |
| *A61B 5/1455* | (2006.01) |
| *H01L 31/18* | (2006.01) |
| *A61B 5/145* | (2006.01) |
| *G01N 21/39* | (2006.01) |
| *G01N 21/77* | (2006.01) |

(52) U.S. Cl.
CPC ........ *A61B 5/1455* (2013.01); *A61B 5/14532* (2013.01); *G01N 21/39* (2013.01); *G01N 21/7743* (2013.01); *H01L 31/18* (2013.01); *A61B 2562/0233* (2013.01); *A61B 2562/12* (2013.01)

(58) Field of Classification Search
CPC .......... G01J 1/0407; G01J 1/4228; G01J 1/08; G01N 21/0303; G01N 21/27; H01L 31/18; A61B 5/14532; A61B 5/1455
USPC ........................................ 250/552; 372/50.21
See application file for complete search history.

(56) References Cited

U.S. PATENT DOCUMENTS

| | | | |
|---|---|---|---|
| 2003/0021322 A1* | 1/2003 | Steinle | H01S 5/183 372/50.21 |
| 2007/0002327 A1* | 1/2007 | Zhou | A61B 3/102 356/456 |
| 2011/0262307 A1* | 10/2011 | Packirisamy | G01N 21/05 422/82.08 |
| 2014/0080729 A1 | 3/2014 | Grego et al. | |
| 2014/0353583 A1* | 12/2014 | Chang-Hasnain | H01L 31/02327 257/14 |

OTHER PUBLICATIONS

Brundrett et. al. "Normal-incidence guided-mode resonant grating filters: design and experimental demonstration", Optical Letters, vol. 23, No. 9, May 1, 1998, 3 pages.
(Continued)

*Primary Examiner* — Seung C Sohn
(74) *Attorney, Agent, or Firm* — Gordon & Rees LLP

(57) ABSTRACT

An optical sensor for detecting chemical, biochemical or biological substances includes a laser and a semiconductor chip. The sensor includes at least one photodetector and at least one high-contrast grating that are monolithically integrated in the semiconductor chip. The high-contrast grating is configured to optically couple radiation emitted by the laser into the photodetector. The coupling behavior of the high-contrast grating depends on the optical properties of external substances that are brought near to or in contact with the high-contrast grating.

16 Claims, 7 Drawing Sheets

(56) References Cited

OTHER PUBLICATIONS

Carlos F. R. Mateus et al., "Compact Label-Free Biosensor Using VCSEL-Based Measurement System", IEEE Photonics Technology Letters, vol. 16, No. 7, pp. 1712-1714, Jul. 2004.
Connie J. Chang-Hasnain and Weijian Yang, "High-contrast gratings for integrated optoelectronics", Advances in Optics and Photonics, No. 4, pp. 379-440, 2012.
Jeremy J. Ramsden, "Optical biosensors", Journal of Molecular Recognition, vol. 10, pp. 109-120, 1997.
Liu et. al. "Two dimensional analysis of finite size high-contrast gratings for applications in VCSELs", Optics Express, vol. 22, No. 10, May 19, 2014, 8 pages.
Sonia Grego et al., "Wavelength interrogation of grating-based optical biosensors in the input coupler configuration", Sensors and Actuators, vol. B, No. 131, pp. 347-355, 2008.
Xing Wei and Sharon M. Weiss, "Guided mode biosensor based on grating coupled porous silicon waveguide", Optics Express, vol. 19, No. 12, pp. 11330-11339, Jun. 6, 2011.
Ye Zhou et al., "Surface-normal emission of a high-Q resonator using a subwavelength high-contrast grating", Optics Express, vol. 16, No. 22, pp. 17282-17287, Oct. 27, 2008.
Yongkang Gao et al, "Plasmonic interferometric sensor arrays for high performance label-free biomolecular detection", Lab on a Chip, vol. 13, No. 24, pp. 4755-4764, Dec. 21, 2013.
Yuze Sun and Xudong Fan, "Optical ring resonators for biochemical and chemical sensing", Anal Bioanal Chem, No. 399, pp. 205-211, 2011.
Zhu et. al., "Novel high efficiency vertical coupler using subwavelength high contrast grating", Optical Society of America, 2011, 2 pages.

\* cited by examiner

OPTICAL SENSOR FOR DETECTING CHEMICAL, BIOCHEMICAL OR BIOLOGICAL SUBSTANCES

The present invention relates to sensors and methods of fabricating an optical sensor.

BACKGROUND OF THE INVENTION

Portable, low-power, label-free, real-time, compact, high-sensitivity, high-throughput, and cost-effective assay tools are highly attractive and can be widely used in environmental monitoring, homeland security, biomedicine, biochemistry and pharmacy. A label-free sensor is an assay tool that enables direct biochemical and chemical detection, and it is generally desirable due to its non-intrusive nature of detection different from the sensor with labelling with compounds (e.g. fluorescent, radioactive, and colorimetric).

Optical sensors [1] for biochemicals or chemicals are a kind of label-free sensors using light as the detection mechanism. They comprise optical transducers to convert the presence or the amount of chemical or biological agents into quantitatively measurable optical signals, such as phase, amplitude, and frequency. These optical sensors have many advantages, such as less complexity due to no labelling, in situ real-time monitoring, and high sensitivity.

There are several optical sensors for biochemical or chemical sensing with noticeable success, for example based on surface plasmon resonances [2], input/output grating couplers [3,4,5], evanescent wave devices [6], and guided mode resonance (GMR) [7]. Although optical sensors using these methods are very sensitive with discrete optical detection units, they are still bulky and expensive. Optical sensors based on surface plasmon resonances require both a discrete optical source and an optical detection unit. Grating-coupler-based optical sensors have inherent difficulties, due to their operation principle, to simultaneously integrate the optical source and the optical detector. Optical sensors based on evanescent waves, such as ring resonators, require expensive external tunable diode lasers. GMR optical sensors use a discrete detector to monitor the peak shift in the reflectivity spectrum.

Infinite-size high-contrast gratings (HCGs) always have a broadband high reflectivity, and can serve as mirrors. Finite-size HCGs demonstrate a Fano resonance with a very high Q value, and a kind of HCG-based biosensor was proposed [8]. This HCG-based biosensor, like above-mentioned optical sensors, is very bulky, expensive and hard to handle, because it requires a discrete optical detection unit to monitor the peak shift in the reflectivity spectrum.

TDLAS (Tunable Diode Laser Absorption Spectroscopy) requires expensive laser diodes of very special wavelengths and of very high cost. The required optics for higher sensitivity are very costly. TDLAS works well in the gas-phase but has severe problems with liquids.

OBJECTIVES OF THE PRESENT INVENTION

An objective of the present invention is to provide a sensor that can be manufactured at low costs.

A further objective of the present invention is to provide a method for manufacturing sensors at low costs.

BRIEF SUMMARY OF THE INVENTION

An embodiment of the invention is directed to an optical sensor for detecting chemical, biochemical or biological substances, the sensor comprising a laser and a semiconductor chip. At least one photodetector and at least one high-contrast grating are monolithically integrated in said same chip. The high-contrast grating is configured to optically couple radiation emitted by the laser into the photodetector. The coupling behaviour of said high-contrast grating depends on the optical properties of external substances that are brought near to or in contact with the high-contrast grating.

The chip is preferably a label-free sensor which detects substances without labelling.

The chip preferably comprises a semiconductor sensor layer, a first section of said sensor layer forming a receiving portion of said photodetector and a second section of said sensor layer forming the high-contrast grating.

The high-contrast grating may at least partly lay bare and may thus allow being brought in direct contact with external substances.

The first section of said sensor layer is preferably vertically sandwiched between a p-doped semiconductor layer and a n-doped semiconductor layer, alternatively using an evanescently coupled p-i-n photodetector or metal-semiconductor-metal (MSM) photodetector.

The high-contrast grating may be configured to guide a low-Q guided mode. The guiding behaviour of the high-contrast grating with respect to the low-Q guided mode is preferably dependent on the optical properties of the environment around the high-contrast grating.

The laser is preferably configured to excite said low-Q guided mode.

The photodetector is preferably configured to detect said low-Q guided mode.

The low-Q guided mode is preferably capable of transforming all or at least a part of the normal or oblique incidence optical radiation of the laser into the in-plane direction of the high-contrast grating.

The low-Q guided mode is preferably excited by the nonzero angular components of the normally or obliquely incident radiation.

Further, the laser is preferably tunable and preferably allows adapting the wavelength of the emitted radiation with respect to the wavelength of the low-Q guided mode.

The high-contrast grating may consist of or comprise bars made of II-VI semiconductor material, III-V semiconductor material, or semiconductor material of group IV of the periodic system.

The bars preferably have a refractive index between 2.8 and 4.2. The bars are preferably completely exposable to the external substances. Alternatively, the bars may only be partly exposable with the remaining part or parts of the bars being surrounded by low-index material having a refractive index between 1 and 2.

The high-contrast grating preferably provides $0^{th}$-order diffraction and has a grating period between $\lambda/n_{low}$ and $\lambda/n_{high}$, wherein $\lambda$ describes the wavelength of the laser's radiation in vacuum, $n_{low}$ describes the refractive index of low-index material or air that surrounds the high-contrast grating, and $n_{high}$ describes the refractive index of said bars.

The high-contrast grating is preferably configured to initiate polarization dependence of the radiation that is directed towards the photodetector.

The laser is preferably a VCSEL that is integrated inside said semiconductor chip beneath the high-contrast grating.

A sacrificial layer preferably carries the photodetector. To this end, said sacrificial layer may be locally removed between the high-contrast grating and the laser.

The laser preferably provides wavelength tuning ability and is configured to emit polarization-stable light.

Furthermore, the sensor may comprise a plurality of sensor elements, each sensor element comprising at least one photodetector and at least one high-contrast grating, wherein all photodetectors and all high-contrast gratings of said plurality of sensor elements are monolithically integrated in the same chip.

The sensor elements may be arranged in 1 dimension or 2 dimensions.

A further embodiment of the present invention relates to a method of fabricating an optical sensor for detecting chemical, biochemical or biological substances. The method comprises the step of monolithically integrating at least one photodetector and at least one high-contrast grating in the same chip.

A further embodiment of the present invention relates to a monolithically integrated optical sensor for detecting chemical, biochemical or biological substances, the sensor comprising a semiconductor chip, said chip comprising

- a VCSEL laser monolithically integrated in said semiconductor chip wherein a semiconductor sensor layer of said semiconductor chip is located above the laser;
- at least one photodetector being monolithically integrated in said semiconductor chip, a receiving portion of said photodetector being formed by a first section of said sensor layer;
- at least one high-contrast grating being formed in a second section of said sensor layer, wherein the high-contrast grating is configured to optically couple radiation emitted by the laser into the receiving portion of said photodetector;
- wherein said high-contrast grating at least partly lies bare and allows being brought near to or in direct contact with external substances; and
- wherein the first section of said sensor layer is vertically sandwiched between a p-doped semiconductor layer and a n-doped semiconductor layer, said p-doped semiconductor layer and said n-doped semiconductor layer being monolithically integrated layers of said semiconductor chip, or alternatively the first section of said sensor layer is monolithically integrated with an evanescently coupled p-i-n photodetector or MSM photodetector.

With respect to the latter embodiment, the high-contrast grating is preferably configured to guide a low-Q guided mode, the guiding behaviour of the high-contrast grating with respect to the low-Q guided mode being dependent on the optical properties of the external substances that are brought in contact with the high-contrast grating. The laser is preferably configured to excite said low-Q guided mode; and the photodetector is preferably configured to detect said low-Q guided mode.

BRIEF DESCRIPTION OF THE DRAWINGS

In order that the manner in which the above-recited and other advantages of the invention are obtained will be readily understood, a more particular description of the invention briefly described above will be rendered by reference to specific embodiments thereof which are illustrated in the appended figures. Understanding that these figures depict only typical embodiments of the invention and are therefore not to be considered to be limiting of its scope, the invention will be described and explained with additional specificity and detail by the use of the accompanying drawings.

DETAILED DESCRIPTION OF THE PREFERRED EMBODIMENTS

The preferred embodiments of the present invention will be best understood by reference to the drawings, wherein identical or comparable parts are designated by the same reference signs throughout.

It will be readily understood that the present invention, as generally described herein, could vary in a wide range. Thus, the following more detailed description of the exemplary embodiments of the present invention, is not intended to limit the scope of the invention, as claimed, but is merely representative of presently preferred embodiments of the invention.

Figure 1:
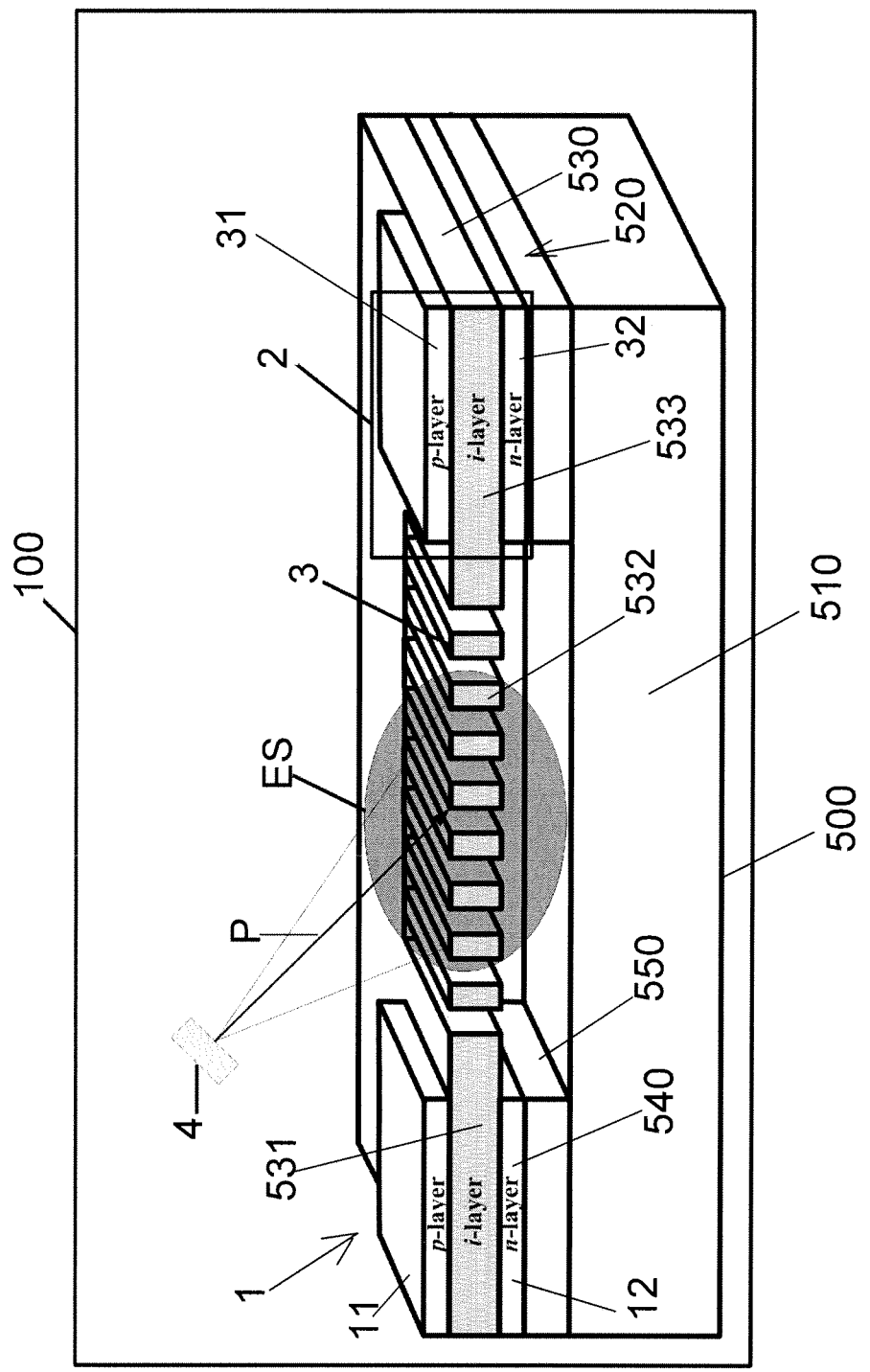
FIG. 1 shows a first exemplary embodiment of an optical sensor for detecting chemical, biochemical or biological substances.

FIG. 1 shows a first exemplary embodiment of an integrated HCG-based optical sensor 100 for detecting chemical, biochemical or biological substances ES.

The sensor 100 comprises a first on-chip p-i-n photodiode detector 1 (photodetector), a second on-chip p-i-n photodiode detector 2 (photodetector), and a high-contrast grating 3, hereinafter also referred to as HCG 3, and a laser, for instance a vertical emitting laser 4, hereinafter also referred to as VCSEL 4.

The first and second on-chip p-i-n photodiodes 1 and 2 as well as the high-contrast grating 3 are monolithically integrated in the same semiconductor chip 500. The semiconductor chip 100 comprises a substrate 510 and a layer stack 520 of semiconductor layers. The layer stack 520 is located on the upper surface of the substrate 500.

The layer stack 520 comprises a semiconductor sensor layer 530.

A first section 531 of the sensor layer 530 forms a receiving portion of the first on-chip p-i-n photodiode detector 1. The first section 531 is vertically sandwiched between a p-doped semiconductor layer 11 and a n-doped semiconductor layer 12 of the first on-chip p-i-n photodiode detector 1.

A second section 532 of the sensor layer 530 forms the high-contrast grating 3. The second section 532 of the sensor layer 530 and therefore the high-contrast grating 3 lay bare and allow being brought in direct contact with the external substances ES. The high-contrast grating 3 is configured to guide a low-Q guided mode that is generated by the VCSEL 4.

A third section 533 of the sensor layer 530 forms a receiving portion of the second on-chip p-i-n photodiode detector 2. The third section 533 is vertically sandwiched between a p-doped semiconductor layer 31 and a n-doped semiconductor layer 32 of the second on-chip p-i-n photodiode detector 2.

The n-doped layers 12 and 32 of the first and second on-chip p-i-n photodiode detectors 1 and 2 are sections of a first sacrificial layer 540 that is locally removed below the high-contrast grating 3. A second sacrificial layer 550 is located beneath the first sacrificial layer 540. The second sacrificial layer 550 carries the first and second on-chip p-i-n photodiode detectors 1 and 2, and is also locally removed below the high-contrast grating 3.

The sensor 100 may operate as follows:

The VCSEL 4 generates radiation P which may couple into the high-contrast grating 3. The coupling efficiency depends on the surrounding of the high-contrast grating 3. If substances ES are present, the optical properties of these substances influence the coupling behaviour of the high-contrast grating 3 and therefore the amount of radiation which may be detected by both on-chip p-i-n photodiode detectors 1 and 2. In consequence, one may detect external substances ES by evaluating the photocurrents that are provided by the on-chip p-i-n photodiode detectors 1 and 2.

Figure 2:
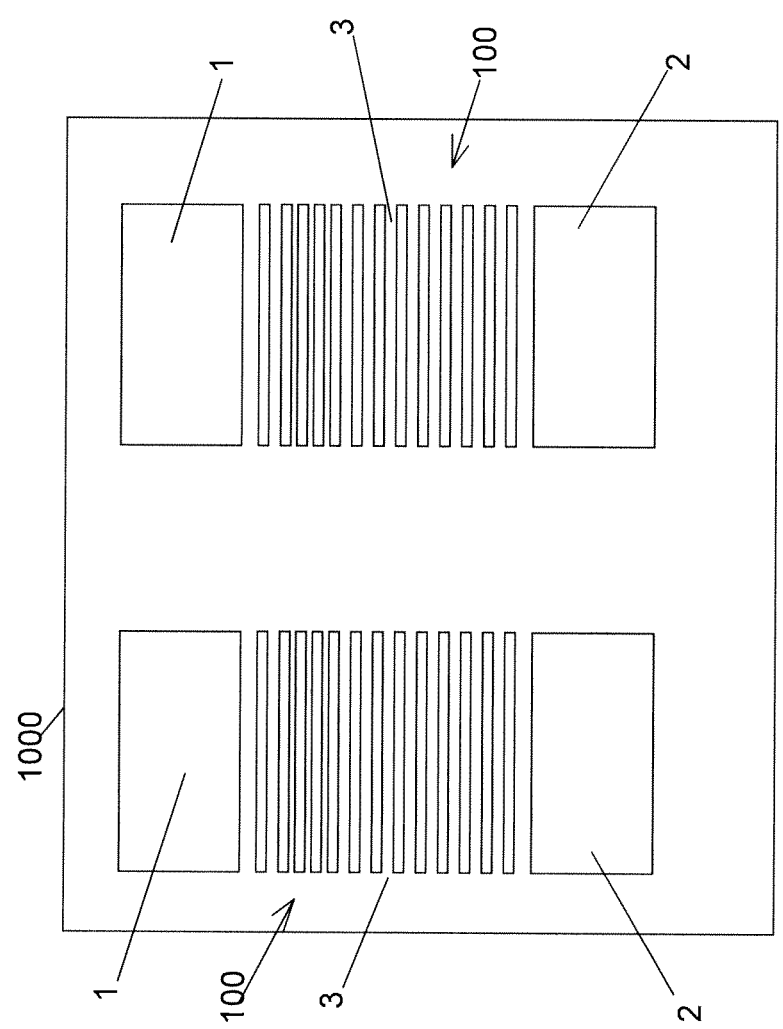
FIG. 2 shows an exemplary embodiment of a 1-dimensional sensor array, which comprises sensors as shown in FIG. 1.

FIG. 2 shows a graphical representation of a top view of a first exemplary embodiment of a 1-dimensional integrated HCG-based optical sensor array (1×2) 1000, which may be composed of two integrated HCG-based optical sensors 100 as illustrated in FIG. 1.

Figure 3:
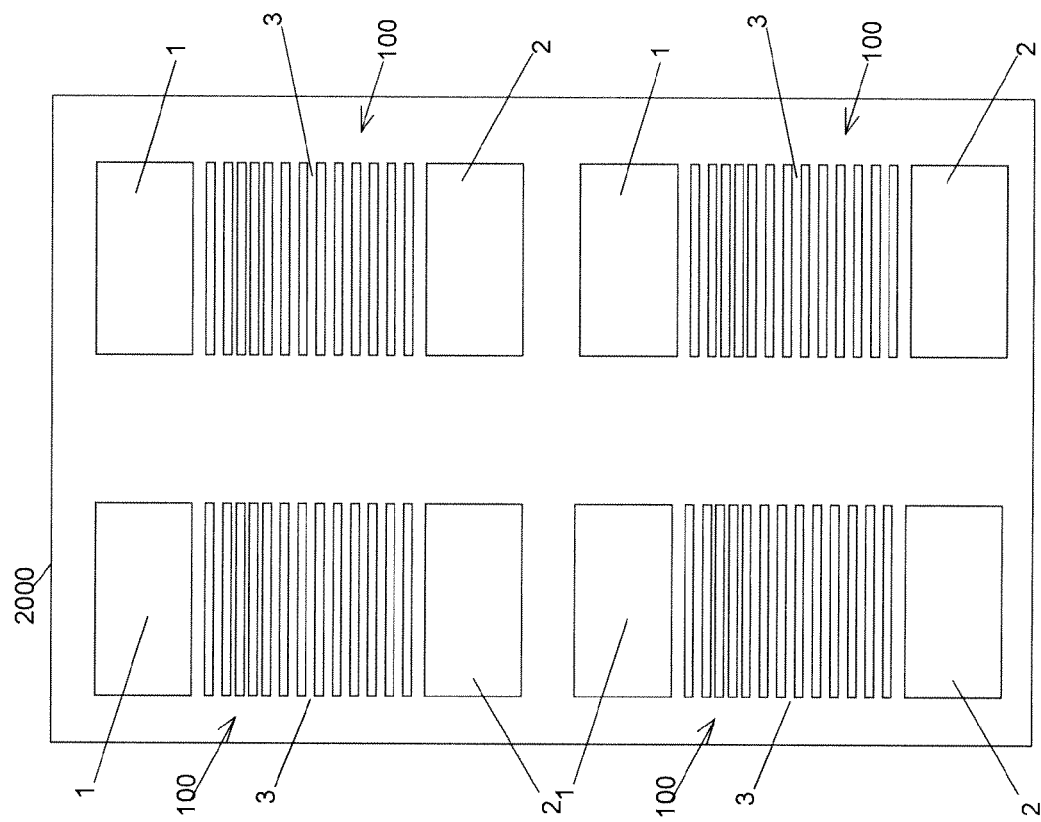
FIG. 3 shows an exemplary embodiment of a 2-dimensional sensor array, which comprises sensors as shown in FIG. 1.

FIG. 3 shows a graphical representation of a top view of a first exemplary embodiment of a 2-dimensional integrated HCG-based optical sensor array (2×2) 2000, which is composed of four integrated HCG-based optical sensors 100 as illustrated in FIG. 1.

Figure 4:
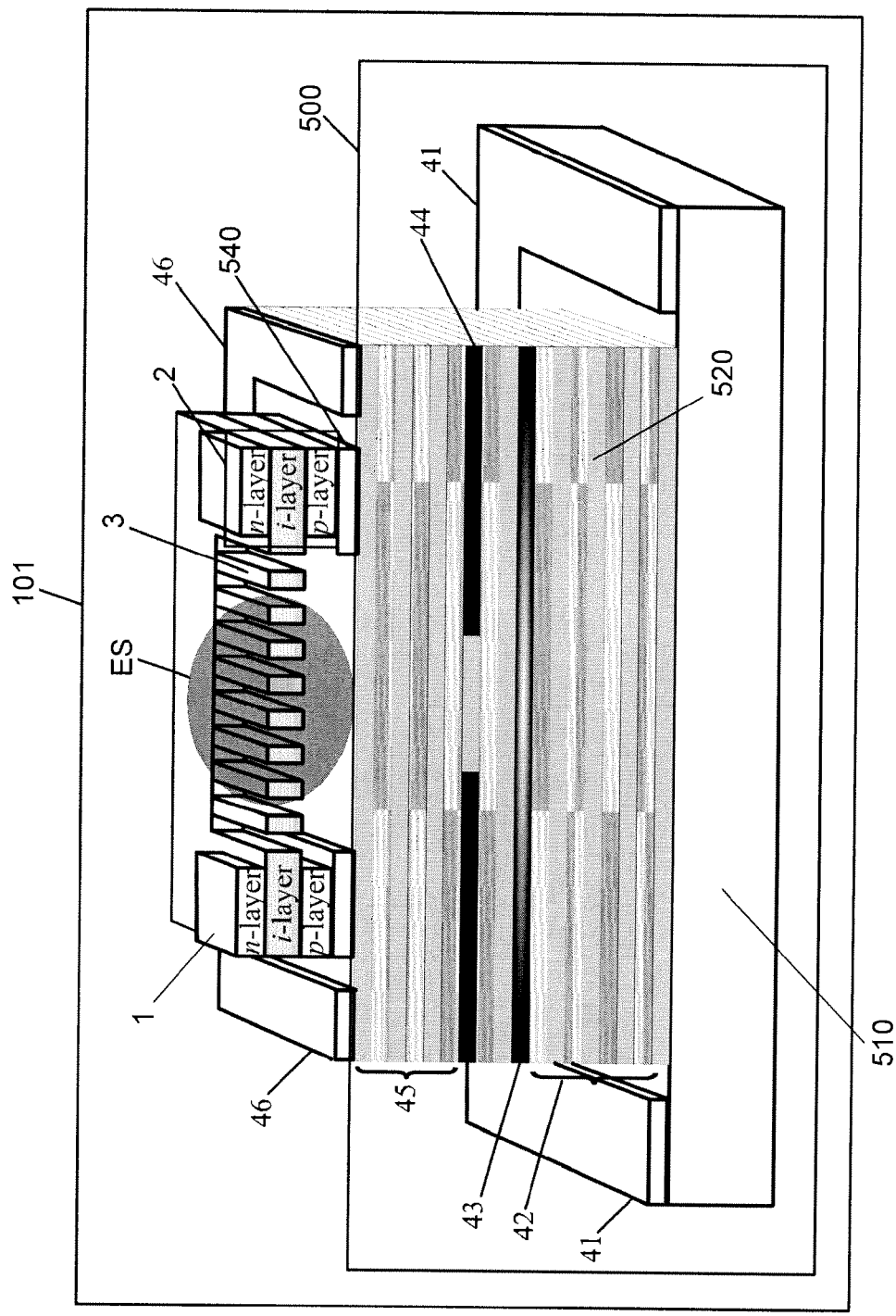
FIG. 4 shows a further exemplary embodiment of an optical sensor for detecting chemical, biochemical or biological substances.

FIG. 4 shows a second exemplary embodiment of an integrated HCG-based optical sensor 101 for detecting chemical, biochemical or biological substances ES. The sensor 101 comprises a first on-chip p-i-n photodiode detector 1, a second on-chip p-i-n photodiode detector 2, a high-contrast grating 3, and a VCSEL 4.

In contrast to the embodiment shown in FIG. 1, the VCSEL 4 is monolithically integrated in the semiconductor chip 500, preferably in its layer stack 520. The integrated VCSEL 4 comprises or is composed of an n-contact 41, an n-doped DBR (distributed Bragg reflector) 42, an active layer 43, an oxide aperture layer 44, a p-doped DBR 45, and a p-contact 46.

Figure 5:
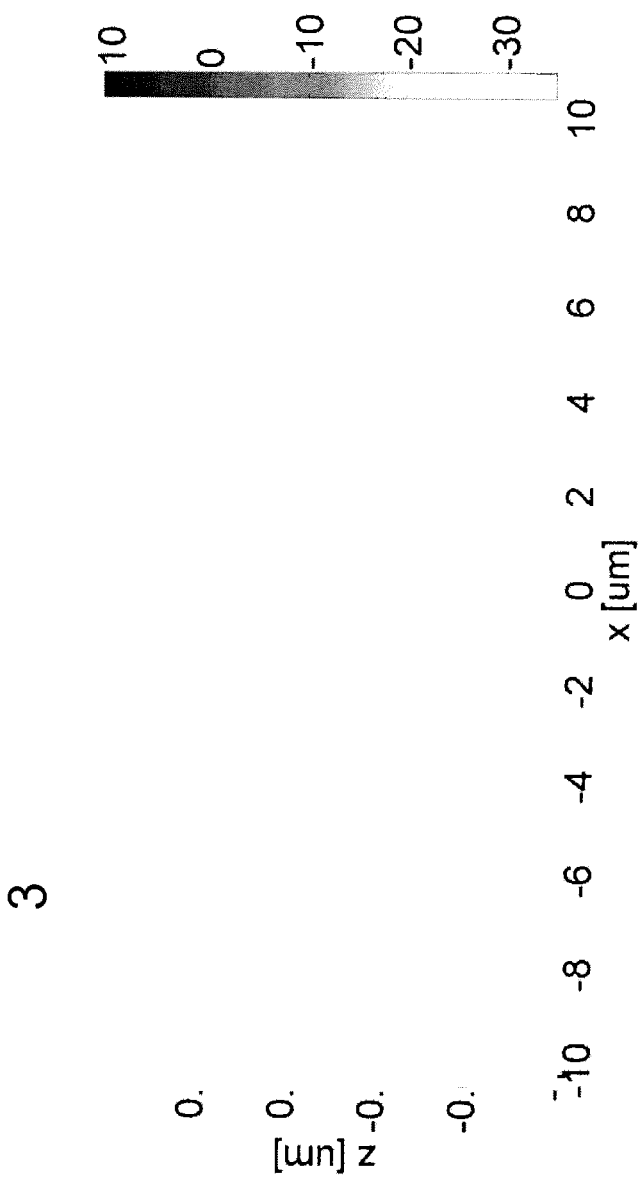
FIG. 5 shows the field distribution of the guided mode in the optical sensor of FIG. 4.

FIG. 5 shows in an exemplary fashion the field distribution of the guided mode with even symmetry in the high-contrast grating 3 of FIG. 4 under a finite-size incident wave. When the finite-size Gaussian wave is incident on the high-contrast grating 3, the guided mode in the HCG region is excited by the nonzero angular components of the finite-size Gaussian wave. Because of this guided mode, a part of the incident wave is reflected, and also a part of the incident wave is transmitted. The guided mode at the HCG region can be also coupled into the fundamental mode of the slab (waveguide). Thus the in-plane propagating wave in the slab provides the opportunity to integrate the on-chip p-i-n photodiode detectors 1 and 2 in the same (sensor) layer as the high-contrast grating 3.

Figure 6:
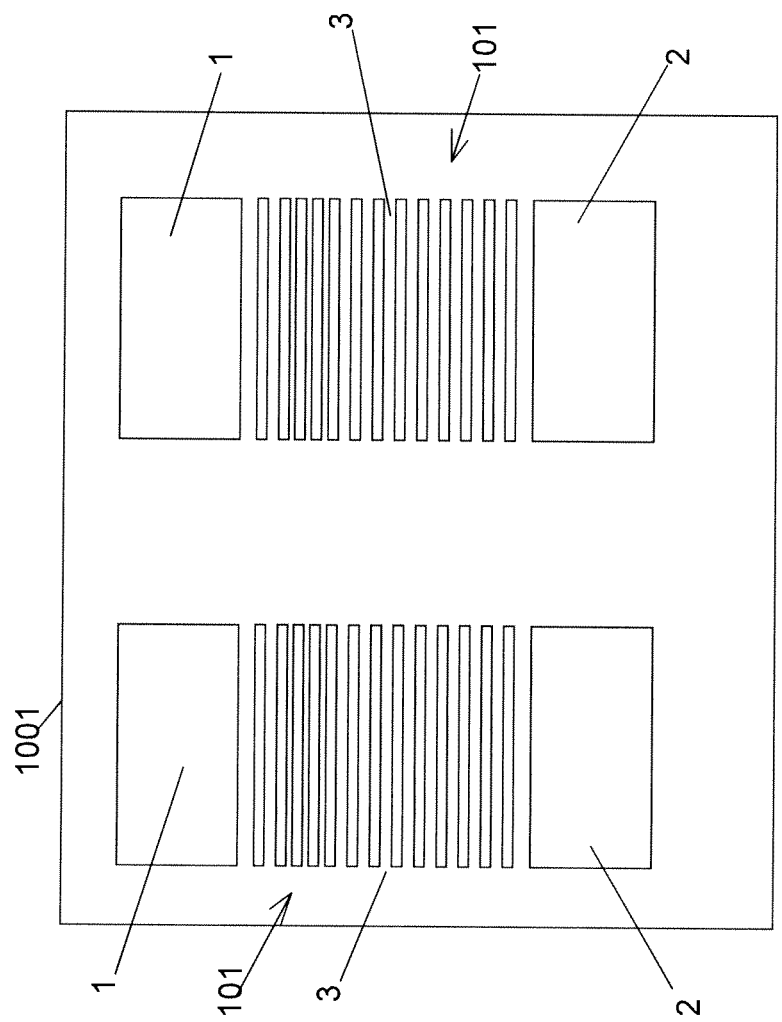
FIG. 6 shows an exemplary embodiment of a 1-dimensional sensor array, which comprises sensors as shown in FIG. 4.

FIG. 6 shows a graphical representation of a top view of a second exemplary embodiment of a 1-dimensional integrated HCG-based optical sensor array (1×2) 1000. The sensor array 1001 may be composed of two integrated HCG-based optical sensors 101 as illustrated in FIG. 4.

Figure 7:
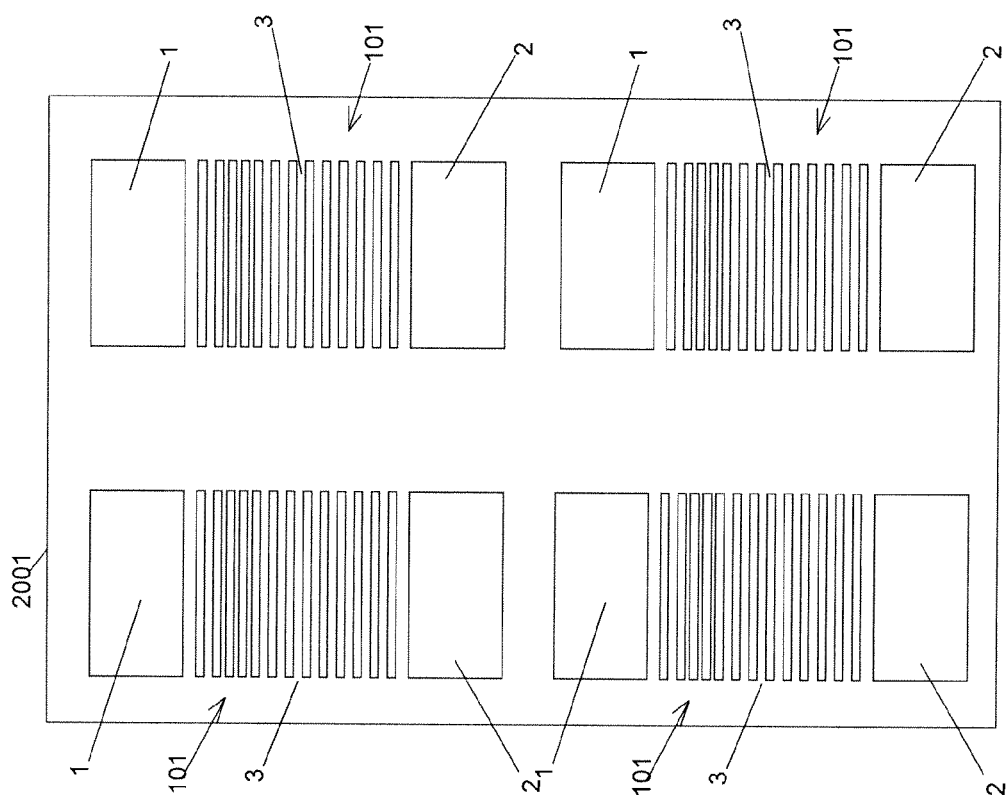
FIG. 7 shows an exemplary embodiment of a 2-dimensional sensor array, which comprises sensors as shown in FIG. 4.

FIG. 7 shows a graphical representation of a top view of a second exemplary embodiment of a 2-dimensional integrated HCG-based optical sensor array (2×2) 2001. The sensor array 2001 may be composed of four integrated HCG-based optical sensors 101 as illustrated in FIG. 4.

The sensors 100 and the sensor arrays 1000 as described above may be used to detect glucose. Continuous glucose monitoring helps diabetes mellitus patients stabilize their glucose levels, leading to improved patient health. Compact and cost-effective optical sensors for glucose monitoring improve patient quality of life and add savings for healthcare systems. The disclosed integrated HCG-based optical sensors can be applied to monitor the blood glucose level.

The finite-size HCG as shown in FIG. 1 preferably has a period of 380 nm, duty cycle (HCG bar width to period) is preferably 13/19, and the thickness is preferably 235 nm. The finite-size HCG bars are preferably composed of $Al_{0.6}Ga_{0.4}As$ (refractive index is 3.2). The integrated HCG-based optical sensor is preferably exposed to different concentrations for glucose, and the wavelengths of the low-Q guided modes are preferably measured by the p-i-n photodiode. For comparison, water is also detected.

The following Table 1 shows the calculated wavelengths of the guided mode. Different concentrations of glucose have different refractive indices. The peak wavelength of the low-Q guided mode of the finite-size HCG in the optical sensor shifts when the concentration of glucose varies. The concentration variation of glucose can be identified by the integrated p-i-n photodiode detector in real time. The disclosed integrated HCG-based optical sensor for glucose monitoring is very compact, portable, and cost-effective for diabetes mellitus patients.

TABLE 1

| Solution | Refractive index | Peak wavelength [nm] | Shift [nm] |
| --- | --- | --- | --- |
| Water | 1.333 | 859.5 | 0 |
| Glucose, 12 mg/ml | 1.346 | 863.3 | 3.8 |
| Glucose, 20 mg/ml | 1.356 | 866.1 | 6.6 |
| Glucose, 30 mg/ml | 1.370 | 870.1 | 10.6 |

The embodiments as presented above in an exemplary fashion with reference to FIGS. 1-6 may have one or more of the following features:

The finite-size beam from the VCSEL 4 can provide non-zero angular components and excite the low-Q guided mode in the finite-size HCG 3. The VCSEL 4 may provide single-mode and polarization-stable output light.

The single-mode operation of the VCSEL 4 can be realized by optimizing the oxide aperture 44. The polarization-stable operation of the VCSEL 4 can be realized by the weak feedback of the finite-size HCG 3.

The wavelength of the VCSEL 4 can be tuned by current or by voltage (with micro-electro-mechanical system (MEMS) technology) to the wavelength of the low-Q guided mode in the finite-size HCG 3.

The finite-size HCG 3 preferably has bars fully immersed in air. The period of the finite-size HCG 3 is preferably less than the wavelength of the VCSEL 4. The finite-size HCG 3 preferably provides weak feedback to help the VCSEL 4 realize polarization-stable operation. The finite-size HCG 3 preferably has a low-Q guided mode which transforms all or part of the normal or oblique incidence light into the in-plane direction. The wavelength of the low-Q guided mode preferably shifts when the biochemical or chemical substances ES around the finite-size HCG bars change. The on-chip p-i-n photodiode detectors 1 and 2 are preferably integrated in the same layer 530 as the finite-size HCG 3. The on-chip photodiode detectors 1 and 2 preferably detect optical intensity of the low-Q guided mode in the finite-size HCG 3. The wavelength shift of the low-Q guided mode in the finite-size HCG 3 can be identified according to the driving current or driving voltage of the VCSEL 4 and the current of the photodiode detectors 1 and 2.

With respect to the HCGs, the grating bars are preferably fully immersed in low-index material resulting in a high index contrast. The grating bars may be made of semiconductors with a typical refractive index of from 2.8 to 4.2. The low-index material can be air and/or oxide layers (refractive index: 1 to 2). When the grating period is between the wavelength in low-index material and the wavelength in high-index material, only $0^{th}$-order diffraction occurs. The HCG can have a high reflectivity with a broad band due to the dual-mode destructive interference when the plane wave is normally incident [9]. However, when the plane wave is off-normally incident for infinite-size HCGs, low-Q guided modes are excited. The low-Q guided mode can reduce the reflectivity and enhance the transmission in the infinite-size HCG. For a finite-size HCG with a finite-size normally incident wave, the non-zero angular components can excite the low-Q guided modes. The low-Q guided modes can be coupled to the waveguide mode in the in-plane slab besides enhancing the transmission. The finite-size HCG can be modelled as a cavity-waveguide-coupled system, which can not be explained by the phase-matched condition used in [3,5]. To achieve a low-Q guided mode in the finite-size HCG (cavity) coupled to the waveguide mode in the slab (waveguide), the low-Q guided mode and the waveguide mode should satisfy: energy conservation, momentum conservation, and mode symmetry. In a finite-size HCG, there are two kinds of low-Q guided modes: even modes and odd modes. The even modes in the finite-size HCG can be coupled to the fundamental mode in the slab, and the odd mode can be coupled to the $1^{st}$-order mode in the slab. When a chemical or biochemical is present in finite-size HCGs, the low index changes, and the wavelength of the low-Q guided mode shifts. Different from [5] using evanescent wave for sensing (the chemical or biochemical has limited overlap with the guided mode field), the chemical or biochemical has here (i.e. according to the present invention) much more overlap with the low-Q guided mode field in the finite-size HCG (not only on the upper and bottom surfaces, and also on the side surfaces of the grating bars), resulting in a higher sensitivity. Thus integrated and highly-sensitive HCG-based optical sensors and sensor arrays can be realized for chemical and biochemical sensing.

As pointed out above, embodiments of the present invention are directed to an apparatus and a method of detecting biomolecular interactions, biochemicals, and chemicals using integrated HCG-based optical sensors without labelling. The apparatus may comprise a finite-size HCG with very specific properties defined by the geometry, which transforms all or part of the normal or oblique incidence wave into the in-plane direction. The wavelength of the low-Q guided mode in the finite-size HCG shifts as the refractive index around the bars in the finite-size HCG changes. This apparatus may also include a low-cost and energy-efficient VCSEL as optical source, and an on-chip integrated photodiode detector to detect the wavelength shift of the low-Q guided mode. This shift is extremely sensitive to the change of refractive index of the surrounding media. The re-direction of light makes very cost-effective detection possible. Different from TDLS, a very cheap VCSEL device like a "mouse-VCSEL" can be used. The function is given by the finite-size HCG and can be achieved for any VCSEL wavelength.

Other embodiments of the present invention are directed to an integrated HCG-based optical sensor array which comprises multiple integrated HCG-based optical sensors. This optical sensor array may simultaneously detect multiple biomolecular interactions, biochemicals, and chemicals without labelling to realize high throughput detection.

The sensors and sensor arrays as described above may have one or more of the following features and/or advantages:
  Use of cheap and available VCSEL device possible
  Monolithically integration of VCSEL as optical source possible
  No expensive "classic" optics needed
  Function given by the finite-size HCG only
  Easy integrated detection due to the redirection of light
  Very high sensitivity
  Multiple detections possible integrated in an array operating with identical VCSELs In summary, embodiments of the invention relate to an apparatus and a method of producing integrated high-contrast-grating (HCG)-based optical sensors for biochemical or chemical sensing, which detects biomolecular interactions, biochemicals, and chemicals without labeling. Embodiments of the invention may comprise or consist of a high contrast grating (HCG: e. g. subwavelength grating with high-index (2.8~4.2) bars fully immersed in low-index (1~2) material), an on-chip integrated photodiode detector and a vertical-cavity surface-emitting laser (VCSEL). Further, embodiments may comprise or consist of an integrated HCG-based optical sensor array, which simultaneously detects multiple biochemicals and chemicals without labelling. Embodiments of the present invention may provide portable, low-power, label-free, compact, high-sensitivity, and high-throughput integrated optical sensors.

The invention claimed is:
1. Optical sensor for detecting chemical, biochemical or biological substances, the sensor comprising a laser and a semiconductor chip,
  wherein at least one photodetector and at least one high-contrast grating are monolithically integrated in said same chip,
  wherein the high-contrast grating is configured to optically couple radiation emitted by the laser into the photodetector, and
  wherein the coupling behaviour of said high-contrast grating depends on the optical properties of external substances that are brought near to or in contact with the high-contrast grating,
  wherein the high-contrast grating is configured to have a low-Q guided mode, the guiding behaviour of the high-contrast grating with respect to the low-Q guided mode being dependent on the optical properties of the environment around the high-contrast grating;
  wherein the laser is configured to excite said low-Q guided mode; and
  wherein the photodetector is configured to detect said low-Q guided mode.

2. Optical sensor according to claim 1 wherein said chip comprises a semiconductor sensor layer, a first section of said sensor layer forming a receiving portion of said photodetector and a second section of said sensor layer forming the high-contrast grating.

3. Optical sensor according to claim 2 wherein the high-contrast grating at least partly lays bare and allows being brought in direct contact with external substances.

4. Optical sensor according to claim 2 wherein the first section of said sensor layer is vertically sandwiched between a p-doped semiconductor layer and a n-doped semiconductor layer, or alternatively below an evanescently coupled p-i-n photodetector or MSM photodetector.

5. Optical sensor according to claim 1 wherein the low-Q guided mode is capable of transforming all or at least a part of the normal or oblique incidence optical radiation of the laser into the in-plane direction of the high-contrast grating.

6. Optical sensor according to claim 5 wherein the low-Q guided mode is excited by the nonzero angular components of the normally or obliquely incident radiation.

7. Optical sensor according to claim 6 wherein the laser is tunable and allows adapting the wavelength of the emitted radiation with respect to the wavelength of the low-Q guided mode.

8. Optical sensor according to claim 1 wherein the high-contrast grating comprises bars made of II-VI semiconductor material, III-V semiconductor material, or semiconductor material of group IV of the periodic system.

9. Optical sensor according to claim 8
wherein said bars have a refractive index between 2.8 and 4.2; and
wherein the bars are completely exposable to the external substances or alternatively just partly with the remaining part or parts of the bars being surrounded by low-index material having a refractive index between 1 and 2.

10. Optical sensor according to claim 9 wherein the high-contrast grating provides $0^{th}$-order diffraction and has a grating period between $\lambda/n_{low}$ and $\lambda/n_{high}$ wherein
$\lambda$ describes the wavelength of the laser's radiation in vacuum,
$n_{low}$ describes the refractive index of low-index material or air that surrounds the high-contrast grating, and
$n_{high}$ describes the refractive index of said bars.

11. Optical sensor according to claim 1 wherein the high-contrast grating is configured to initiate polarization dependence of the radiation that is directed towards the photodetector.

12. Optical sensor according to claim 1 wherein the laser is a VCSEL that is integrated inside said semiconductor chip beneath the high-contrast grating.

13. Optical sensor according to claim 12 wherein a sacrificial layer carries the photodetector, said sacrificial layer being locally removed between the high-contrast grating and the laser.

14. Optical sensor according to claim 1 wherein the laser provides wavelength tuning ability and is configured to emit polarization-stable light.

15. Optical sensor according to claim 1 wherein said sensor comprises a plurality of sensor elements, each sensor element comprising at least one photodetector and at least one high-contrast grating, wherein all photodetectors and all high-contrast gratings of said plurality of sensor elements are monolithically integrated in the same chip.

16. Optical sensor according to claim 15 wherein said sensor elements are arranged in 1 dimension or 2 dimensions.

* * * * *